(12) United States Patent
Rolff et al.

(10) Patent No.: US 9,891,202 B2
(45) Date of Patent: Feb. 13, 2018

(54) FOOD PACKAGING ARRANGEMENT

(71) Applicant: Robert Bosch GmbH, Stuttgart (DE)

(72) Inventors: Malte Rolff, Stockelsdorf (DE); Katrin Luckert, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/263,620

(22) Filed: Sep. 13, 2016

(65) Prior Publication Data

US 2017/0074848 A1    Mar. 16, 2017

(30) Foreign Application Priority Data

Sep. 14, 2015 (DE) .................. 10 2015 217 471

(51) Int. Cl.
| | | |
|---|---|---|
| *G01N 33/02* | (2006.01) | |
| *B65D 79/00* | (2006.01) | |
| *C12Q 1/25* | (2006.01) | |
| *G01N 21/76* | (2006.01) | |
| *G01N 21/77* | (2006.01) | |
| *B65D 25/54* | (2006.01) | |
| *B65D 79/02* | (2006.01) | |
| *C12Q 1/22* | (2006.01) | |
| *G01R 31/12* | (2006.01) | |
| *G01N 31/22* | (2006.01) | |

(52) U.S. Cl.
CPC ............. *G01N 33/02* (2013.01); *B65D 25/54* (2013.01); *B65D 79/00* (2013.01); *B65D 79/02* (2013.01); *C12Q 1/22* (2013.01); *C12Q 1/25* (2013.01); *G01N 21/76* (2013.01); *G01N 21/763* (2013.01); *G01N 21/77* (2013.01); *B65D 2203/12* (2013.01); *G01N 31/223* (2013.01); *G01N 2021/7786* (2013.01)

(58) Field of Classification Search
CPC .......... B65D 25/54; B65D 79/00; C12Q 1/25; G01N 21/763; G01R 31/12
See application file for complete search history.

(56) References Cited

U.S. PATENT DOCUMENTS

| | | | | |
|---|---|---|---|---|
| 6,428,748 | B1 * | 8/2002 | Wallach | G01N 21/78 422/421 |
| 6,495,368 | B1 * | 12/2002 | Wallach | G01N 31/221 422/421 |
| 7,785,894 | B2 * | 8/2010 | Smolander | G01N 31/223 116/206 |
| 2004/0115319 | A1 * | 6/2004 | Morris | B65B 25/001 426/231 |
| 2005/0249899 | A1 * | 11/2005 | Bonutti | B32B 27/00 428/35.2 |
| 2007/0172910 | A1 * | 7/2007 | Nolen | B65D 79/02 435/34 |
| 2007/0243618 | A1 * | 10/2007 | Hatchett | G01M 3/38 436/1 |
| 2010/0112680 | A1 * | 5/2010 | Brockwell | A61B 5/07 435/287.9 |
| 2014/0154724 | A1 * | 6/2014 | Reardon | C12Q 1/26 435/25 |

* cited by examiner

*Primary Examiner* — Jennifer Wecker
(74) *Attorney, Agent, or Firm* — Michael Best & Friedrich LLP

(57) ABSTRACT

A food packaging arrangement (1) comprising a packaging (2) and a chemical composition (4) which, by reaction with a breakdown product of the food (3) in question, forms a light-emitting or fluorescent compound or emits light.

14 Claims, 3 Drawing Sheets

FOOD PACKAGING ARRANGEMENT

BACKGROUND OF THE INVENTION

The present invention relates to a food packaging arrangement with which the quality of a food is determinable.

To ensure the food quality and freshness of a perishable food, a best-before date is stated on the food packaging. In spoilage processes, decomposition of the food occurs owing to differing microorganisms. Spoilt foods, that is to say foods containing breakdown products, however, cannot always be reliably visualized without opening the packaging and analyzing the product. This involves dangers for the food consumer, since the spoilage is only visible to the eye in an advanced state.

SUMMARY OF THE INVENTION

The food packaging arrangement according to the invention, overcomes this problem. According to the invention a food packaging arrangement is provided which rapidly and reliably permits a clear statement on the freshness and therefore the quality of a packaged food, without the packaging needing to be opened. The food packaging arrangement permits the assessment of the state of the food, in particular in the case of closed packaging, independently of the best-before date that is estimated in a general manner. Therefore, commerce and the client can decide on the basis of sensory quality how long the food is suitable for consumption.

The food packaging arrangement according to the invention comprises a packaging and a chemical composition which, by reaction with a breakdown product of the food in question, forms a light-emitting or fluorescent compound or emits light. The chemical composition can be a single chemical compound or a group of chemical compounds which, on account of the reactivity thereof, acts as sensor for the quality and freshness of the food. As far as the food is still not subject to any decay, that is to say any breakdown, the chemical composition is unreactive. No reaction of the chemical composition takes place. However, as soon as a breakdown product of the food forms with specific chemical properties, the chemical composition present in the packaging is activated and it reacts with the breakdown product of the packaged food. The reaction is not restricted in detail, but is designed in such a manner that, in the case of reaction as a reaction product, either a light-emitting, that is to say luminescent, compound or a fluorescent compound is formed or else, in the reaction, light in the form of radiation is generated. The light that is transmitted is perceptible visually or by means of a suitable detector, that is to say is determinable at least qualitatively, and advantageously also quantitatively. The packaging in this case is advantageously designed in such a manner that it is permeable to the emitted light. Thus the quality of the food can be determined through the closed packaging without the quality of the food being impaired.

Advantageously, the light is emitted directly in the reaction of the chemical composition with the breakdown product of the food, since this does not require an additional illumination unit, such as, in particular, for exciting to fluorescence. The food packaging arrangement according to the invention permits a simple quality examination of the food, offers high protection and safety for the user or consumer of the food, is inexpensive and is flexibly usable.

According to an advantageous development of the food packaging arrangement according to the invention, the packaging is light-tight. This has a number of advantages. Firstly, it facilitates quantitative analysis of the emitted light or of the fluorescent light, since the light is not radiated on all sides and, at designated regions of the packaging, can be delivered collimated. Secondly, environmental effects, which can lead to a premature breakdown or impairment of the chemical composition, are thereby excluded. The expression "light-tight" is taken to mean in the context of the present invention that the packaging is impermeable to the emitted light or the fluorescent light.

If the packaging is light-tight, the packaging advantageously comprises an exposable window. The emitted light or the fluorescent light can exit in collimated form and be detected through the window. Also, light excited to fluorescence can enter hereby. The window is permeable to the corresponding light and preferably reclosable, that is to say is reversibly exposable. This permits repeated examination of the food quality.

Further advantageously, the food packaging arrangement comprises a buffer and optionally further additives such as, e.g., stabilizers, dispersants and the like. The buffer is a buffer in the chemical sense, which serves to stabilize a pH range and also for retaining structure and function, e.g. of proteins. Unwanted side reactions not only of the chemical composition but also of the breakdown product can be prevented hereby. In addition, the buffer can serve for moistening the chemical composition, and therefore facilitate the reaction between the chemical composition and the breakdown product.

In order to reduce side reactions or premature breakdown of the chemical composition, the chemical composition is integrated into the packaging in such a manner that it is not directly in connection with the food, but is accessible to the breakdown product of the food. This means, in other words, that the chemical composition is present in a closed region which is connected via an intermediate space with the region of the packaging containing the food and therefore also the breakdown product of the food. The breakdown product of the food can therefore pass via the intermediate space to the chemical composition. Since the breakdown products generally are volatile or liquid compounds, in the case of spatial separation of the chemical composition, this nevertheless is readily accessible by diffusion. The spatial separation additionally prevents impairment of the food.

Advantageously, the buffer is also separate from the food, that is to say is not in direct connection with the food.

A further advantageous development is characterized in that the chemical composition is present bound to a support. As a result, the reaction with the breakdown product can be restricted locally and the light emission and/or fluorescence can be collimated. In addition, it is advantageous that the components required for the reaction can be initially charged collectively, with the exception of the breakdown product, at one point. The appearance of the breakdown product starts the reaction. This increases the reliability of the statement on the qualitative quality of the food.

In this case it is advantageous that the support is a semipermeable membrane that is permeable to the breakdown product of the food in question. Thus, the chemical composition can be stabilized locally (e.g. by buffer salts, pH) and simultaneously kept separate from the food. Unwanted side reactions or a premature breakdown of the chemical composition are effectively prevented thereby.

For simplification of the structure of the packaging, the support is a region of the packaging itself.

Owing to the reliability of the reaction with breakdown products of foods, the chemical composition comprises an aldehyde-specific compound, that is to say a compound that reacts selectively with aldehydes. Aldehydes, that is to say alkanals and including aliphatic alkanals, may be found as breakdown products in diverse foods, in particular foods containing animal proteins, such as, e.g., meat products and sausage products. Aldehyde-specific compounds are distinguished by rapid and highly-specific reaction with the breakdown product aldehyde and are harmless to consumers.

Particularly preferably, the chemical composition contains reduced flavin mononucleotide (FMN). FMN is a compound that can react with aldehydes. Since breakdown products of foods frequently comprise aldehydes, FMN is particularly highly suitable in the context of the present invention. Preferably, the FMN is present covalently bound in the active center of an enzyme. The enzyme in this case has the task of bringing the reactants, that is to say the chemical composition and the breakdown product of the food, and also oxygen, in spatial vicinity, of lowering the activation energy of the reaction of the chemical composition with the breakdown product and of stabilizing transition states. The enzyme is termed an aldehyde-converting enzyme, and appears as a catalyst for the reaction of the composition with the breakdown product of the food. FMN and also enzymes have proved to be non-critical for consumers. The FMN reacts reliably under the effect of oxygen with aldehydes with release of light, that is to say bioluminescence, which is readily detectable and requires no excitation. Reduced FMN oxidizes aldehydes with oxygen to the corresponding acid and in this case is itself oxidized to give the stable compound flavin mononucleotide. The oxygen is itself reduced and converted to water.

Further advantageously, the food packaging arrangement additionally comprises an illumination unit and/or a read-out unit for detecting emitted or fluorescent light.

BRIEF DESCRIPTION OF THE DRAWINGS

Hereinafter, exemplary embodiments of the invention are described in detail with reference to the accompanying drawing. In the drawing.

DETAILED DESCRIPTION

The present invention is described in detail with reference to exemplary embodiments. In this case, only the essential aspects of the invention are shown. All remaining aspects are omitted for the sake of clarity. In the figures, the same reference signs denote the same elements.

Figure 1:
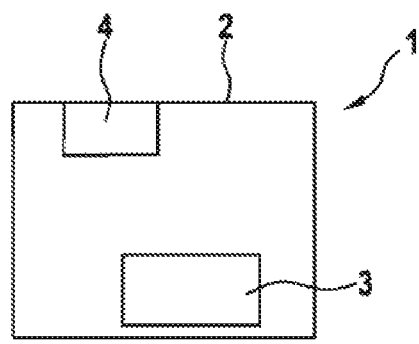
FIG. 1 shows a food packaging arrangement according to a first embodiment in section.

In detail, FIG. 1 shows a sectional view of a food packaging arrangement 1 according to a first embodiment. The food packaging arrangement 1 comprises a packaging 2 for receiving and storing a food 3. The packaging 2 can be, for example, a conventional plastic shell, film packaging or other type of storage unit that can be designed to be both transparent or else colored and thereby light-tight, that is to say light-impermeable. A chemical composition 4 is integrated into the packaging. The chemical composition 4 is able to react with a breakdown product or with breakdown products of the packaged food 3. By the reaction with a breakdown product of the food 3 in question, either a light-emitting or fluorescent compound is formed or light is emitted directly. Particularly advantageously, light is emitted directly in the reaction, since no additional illumination unit, such as, for example, for the excitation to fluorescence, is required therefor. The light can be perceived directly visually. Quantification of the light yield can be facilitated by the food packaging arrangement 1 being transferred to a type of dark chamber, for example a device that seals light-tightly. This is, however, not absolutely necessary. The chemical composition can react not only under chemiluminescence with the breakdown product, but also by self-coloring, that is to say formation of a visible light-emitting compound. This visible light can also be perceived visually and optionally quantified. As a further possibility, the chemical composition 4 can react with reaction with the breakdown product of the food 3 with formation of a fluorescent compound. This has the advantage that the qualitative analysis and quantification of the light yield can be controlled with respect to time and as a result initiated in such a manner that first, for example via an illumination unit, light is radiated into the packaging 2, which light then excites the reaction product of chemical composition and breakdown product of the food to fluorescence, which in turn can be detected.

To facilitate the reaction between the breakdown product of the food 3 and the chemical composition 4, the packaging 2 can in addition comprise a buffer and optionally further additives, wherein the buffer is usually in the liquid form.

The chemical composition 4 is integrated into the packaging 2 and reacts to the breakdown products formed in the course of time from the food 3. Thus, by qualitative and optionally also quantitative analysis of the emitted light or of the fluorescence, a reliable statement on the freshness of the food 3 or on the food quality may be made rapidly and simply without opening the packaging 2.

Figure 2:
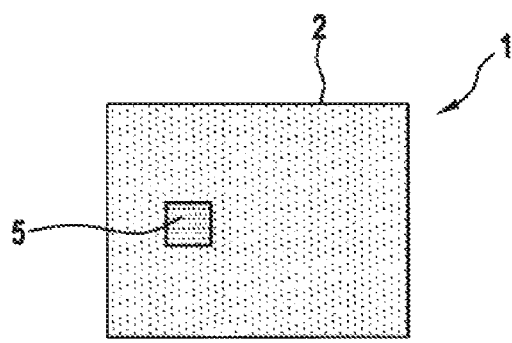
FIG. 2 shows a side view of a food packaging arrangement according to a second embodiment.

FIG. 2 is a side view of a food packaging arrangement 1 according to a second embodiment of the invention. The packaging 2 is designed to be light-tight and therefore light-impermeable and possesses a light-permeable exposable window 5. This window 5 can be covered, for example, by a light-tight adhesive strip which can be taken off in order to expose the window 5. The window 5 itself is a transparent region of the packaging 2. By exposing the window 5, the packaging 2 is not itself opened, but only a region of the packaging 2 is made permeable to light. Thus, the light or fluorescent light emitted by reaction of the chemical composition 4 with the breakdown product of the food 3 can be analyzed in collimated form through the window 5. Preferably, the window 5 is reclosable, in such a manner that repeated monitoring of the food quality can proceed.

Figure 3:
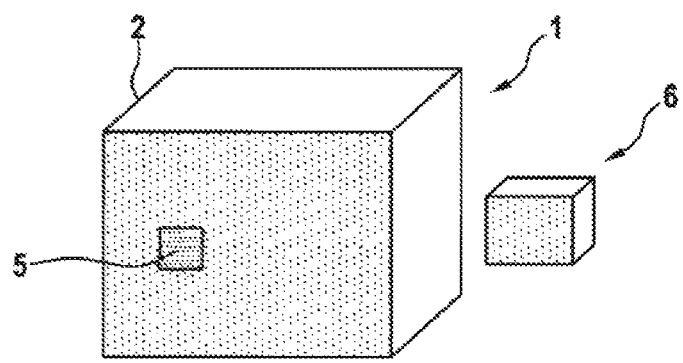
FIG. 3 shows a food packaging arrangement according to a third embodiment and FIG. 4 shows a reaction scheme of a chemical composition.

FIG. 3 shows a food packaging arrangement 1 according to a third embodiment. The food packaging arrangement 1 here further comprises a read-out unit 6, that is to say a detector which qualitatively and quantitatively detects the emitted light or the fluorescence. Preferably, the read-out unit 6 can store a threshold value for the determined amount of light and transmit a warning signal when the threshold value is exceeded.

The food packaging arrangement 1 can additionally have an illumination unit for generating fluorescent light.

Figure 4:
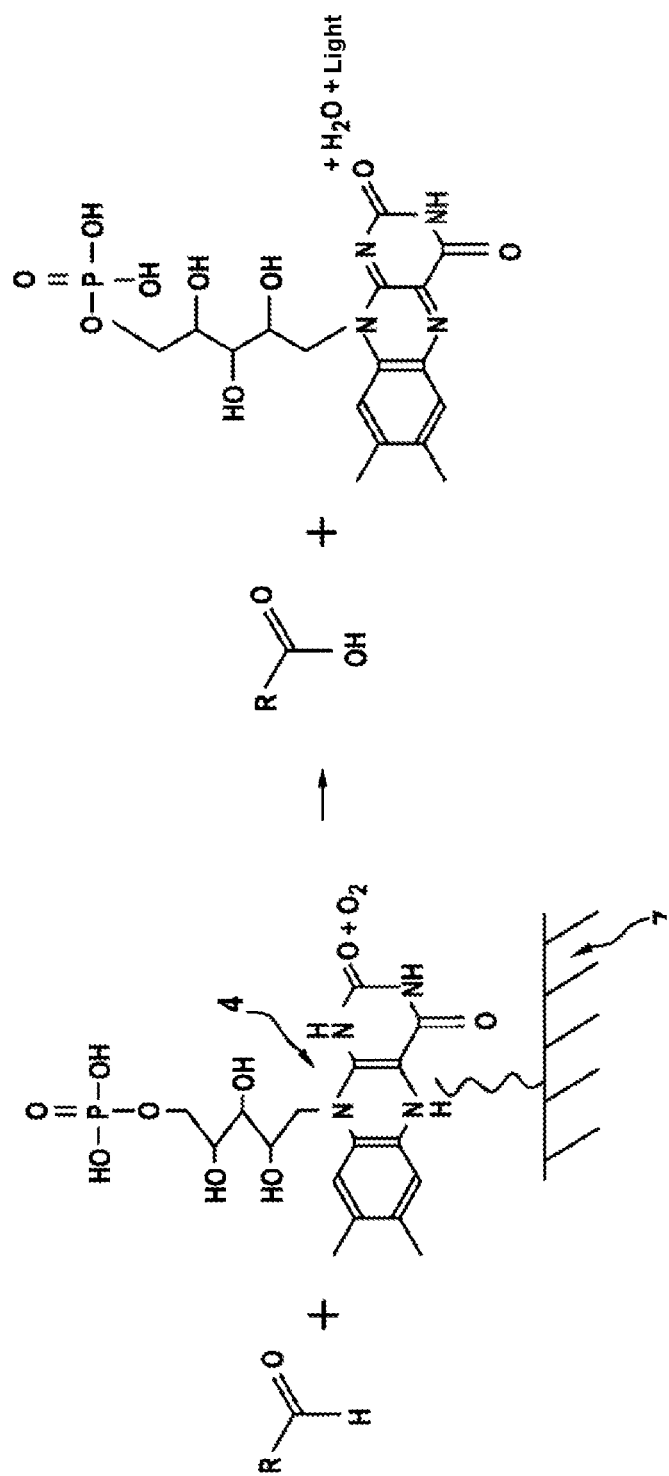

FIG. 4 shows a reaction scheme of a chemical composition 4. The chemical composition 4 is present in the form of a biosensor. The chemical composition 4 comprises an aldehyde-converting enzyme and flavin mononucleotide (FMN). The composition is present in bound form on the surface of a support 7. The binding of the enzyme to the support 7 can take place, for example, by crosslinking the enzyme, optionally with the assistance of further molecules, termed linkers, such as proteins, sugars and the like. The enzyme is situated in a buffered environment, preferably in solution. When a breakdown product of the packaged food appears, for example a long-chain aldehyde, the FMN reacts, catalyzed by the enzyme, in the presence of oxygen with the aldehyde to form a carboxylic acid, wherein FMN in oxidized form and water are formed with liberation of light, that is to say radiation h*v. Per molecule of aldehyde, one molecule of FMN is converted. The amount of light emitted in this case is a percentage of the amount of breakdown product, that is to say aldehyde. Thus, via the quantification of the light yield, conclusions can be drawn on the spoilage rate of the food and a statement can reliably be made on the freshness or food quality.

What is claimed is:

1. A food packaging arrangement, comprising:
    a packaging (2); and
    a chemical composition (4) which is configured to undergo a reaction with a breakdown product of the food (3) in question and to form a light emitting or fluorescent bioluminescent compound or emits light, characterized in that the chemical composition (4) contains reduced flavin mononucleotide, the breakdown product of the food (3) is an aldehyde, and the chemical composition (4) further comprises an aldehyde converting enzyme.

2. The food packaging arrangement according to claim 1, characterized in that the packaging (2) is light-tight.

3. The food packaging arrangement according to claim 2, characterized in that the packaging (2) comprises an exposable window (5) through which light can enter and exit.

4. The food packaging arrangement according to claim 1, additionally comprising a buffer.

5. The food packaging arrangement according to claim 1, characterized in that the chemical composition (4) is integrated into the packaging (2) in such a manner that the chemical composition is not directly in connection with the food (3), but is accessible to the breakdown product of the food (3).

6. The food packaging arrangement according to claim 1, characterized in that the chemical composition (4) is present in bound form on a support (7).

7. The food packaging arrangement according to claim 6, characterized in that the support (7) is a semipermeable membrane that is permeable to the breakdown product of the food (3) in question.

8. The food packaging arrangement according to claim 6, characterized in that the support (7) is a region of the packaging (2).

9. The food packaging arrangement according to claim 1, additionally comprising at least one of an illumination unit and a read-out unit (6) for detecting bioluminescence.

10. The food packaging arrangement according to claim 3, additionally comprising a buffer.

11. The food packaging arrangement according to claim 10, characterized in that the chemical composition (4) is integrated into the packaging (2) in such a manner that the chemical composition is not directly in connection with the food (3), but is accessible to the breakdown product of the food (3).

12. The food packaging arrangement according to claim 11, characterized in that the chemical composition (4) is present in bound form on a support (7).

13. The food packaging arrangement according to claim 12, characterized in that the support (7) is a semipermeable membrane that is permeable to the breakdown product of the food (3) in question.

14. The food packaging arrangement according to claim 12, characterized in that the support (7) is a region of the packaging (2).

* * * * *